United States Patent
Ishikawa et al.

(10) Patent No.: US 9,469,668 B2
(45) Date of Patent: Oct. 18, 2016

(54) MAGNETIC SUBSTANCE

(71) Applicants: IHI CORPORATION, Koto-ku (JP); Yoshihiro Ishikawa, Shinjuku-ku (JP)

(72) Inventors: Yoshihiro Ishikawa, Tokyo (JP); Haruki Eguchi, Koto-ku (JP)

(73) Assignees: IHI CORPORATION, Koto-ku (JP); Yoshihiro Ishikawa, Shinjuku-ku (JP)

( * ) Notice: Subject to any disclaimer, the term of this patent is extended or adjusted under 35 U.S.C. 154(b) by 0 days.

(21) Appl. No.: 14/818,907

(22) Filed: Aug. 5, 2015

(65) Prior Publication Data

US 2015/0336998 A1 Nov. 26, 2015

Related U.S. Application Data

(63) Continuation of application No. PCT/JP2014/052554, filed on Feb. 4, 2014.

(30) Foreign Application Priority Data

Feb. 5, 2013 (JP) .................................. 2013-020939

(51) Int. Cl.
*C07F 15/02* (2006.01)
*H01F 1/42* (2006.01)

(52) U.S. Cl.
CPC ............. *C07F 15/025* (2013.01); *C07F 15/02* (2013.01); *H01F 1/42* (2013.01); *Y10T 428/2982* (2015.01)

(58) Field of Classification Search
CPC ........ H01F 1/42; C07F 15/025; C07F 15/02; Y10T 428/2982
USPC .......................................... 428/402; 556/146
See application file for complete search history.

(56) References Cited

U.S. PATENT DOCUMENTS

| | | | |
|---|---|---|---|
| 9,005,757 B2 * | 4/2015 | Ishikawa | C07C 251/24 128/899 |
| 2009/0169484 A1 * | 7/2009 | Eguchi | A61K 41/0052 424/9.36 |
| 2012/0029167 A1 * | 2/2012 | Ishikawa | A61K 31/135 530/323 |

FOREIGN PATENT DOCUMENTS

| | | |
|---|---|---|
| JP | 2009-173631 A | 8/2009 |
| WO | WO 2008/001851 A1 | 1/2008 |
| WO | WO 2010/058280 A1 | 5/2010 |
| WO | WO 2012/086683 A1 | 6/2012 |
| WO | WO2012/111380 * | 8/2012 |
| WO | WO 2012/111380 A1 | 8/2012 |
| WO | WO2012/172/892 * | 12/2012 |
| WO | WO 2012/172892 A1 | 12/2012 |

OTHER PUBLICATIONS

R.N. Mukherjee et al., "Angle dependence of the properties . . . " Journal of the American Chemical Society, Mar. 1, 1988, vol. 110, 1850-1861.*
International Search Report and Written Opinion issued May 13, 2014 in PCT/JP2014/052554 (with Partial English translation).
R.N. Mukherjee, et al. "Angle Dependence of the Properties of the [Fe$_2$X]$^{4+}$ Bridge Unit (X=O,S): Structures, Antiferromagnetic Coupling, and Properties in Solution" Journal of American Chemical Society, vol. 110, No. 6, 1988, pp. 1850-1861.

* cited by examiner

*Primary Examiner* — Leszek Kiliman
(74) *Attorney, Agent, or Firm* — Oblon, McClelland, Maier & Neustadt, L.L.P.

(57) ABSTRACT

The present disclosure relates to a ferromagnetic substance containing a crystal of a metal complex molecule in which a heterocycle is bonded to metal, the metal of the metal complex molecule is bonded to the metal of another metal complex via oxygen as a electron donor, and the ferromagnetic substance has a ferromagnetic property balanced with stability of crystals based on a metal-electron donor-metal bond angle that is from 130° to 160°. The present disclosure also relates to a drug containing, as a principal component, the crystal of the metal complex molecule.

9 Claims, 4 Drawing Sheets

MAGNETIC SUBSTANCE

CROSS-REFERENCE TO RELATED APPLICATIONS

This application is a Continuation of PCT/JP2014/052554, which was filed on Feb. 4, 2014. This application is based upon and claims the benefit of priority to Japanese Application No. 2013-020939, which was filed on Feb. 5, 2013.

TECHNICAL FIELD

The present disclosure relates to a magnetic substance. Particularly, the disclosure relates to a magnetic substance that is a compound of metal complex organic molecules, regarding which the metal complex organic molecules, such as a magnetic drug or a magnetic material, themselves do not require a magnetic carrier and are capable of exhibiting the magnetic property by themselves.

BACKGROUND ART

The applicant of the present application suggested a metal-salen complex as a ferromagnetic metal complex organic molecule. Regarding this metal-salen complex, electron spins of unpaired electron pairs are oriented either up or down relative to their basic skeleton, so that the metal-salen complex itself can exhibit the ferromagnetic property without any help of a magnetic carrier.

Then, the metal-salen complex is magnetically guided by an external magnetic field. So, when the metal-salen complex is applied to a human or an animal, it is guided by the magnetic field outside the body to a region, to which the magnetic field is locally applied, and retained in that region, and can exhibit its originally retained medicinal effect (such as anticancer) locally in the magnetism-applied region (WO2008/001851). As a result, a therapeutic drug made of the metal-salen complex has the ferromagnetic property by itself without using a magnetic carrier as mentioned above, so that it is useful in exhibiting the stable anticancer effect and reducing the occurrence of side effects.

There is also a metal-salen complex described in WO2012/086683 as the above-described metal-salen complex. When the metal-salen complex is used to make it reach an affected site by means of systemic application and remain in the affected site by the magnetic field, a crystal particle diameter of the metal-salen complex is 1 µm or less so that the metal-salen complex can pass through many capillary vessels; and it is preferable that particles whose crystal particle diameter is from 100 nm to 500 nm inclusive should occupy 70% or more of the entire metal-salen complex. If the particle diameter of the metal-salen complex exceeds 1 µm, there is a possibility that the metal-salen complex may not be able to pass through the capillary vessels. If the particle diameter of the metal-salen complex is less than 100 nm, the ferromagnetic property required for magnetic guidance would not be sufficient.

CITATION LIST

Patent Literature

[PTL 1] WO2008/001851
[PTL 2] WO2012/086683

SUMMARY

Problems to be Solved by the Disclosure

However, as a result of earnest examination by the inventors of the present application, it was found that the magnetic property of the metal-salen complex is not determined only by the crystal particle diameter, but is significantly influenced by a stereo structure of metal-salen complex molecules.

Therefore, it is an object of the present disclosure to clarify the structure of a ferromagnetic metal complex and provide a magnetic substance capable of reliably exhibiting the ferromagnetic property by having that structure.

Means for Solving the Problems

The inventors of the present disclosure analyzed a crystal structure of a metal complex organic substance and analyzed the magnetic property of the metal complex organic substance from the viewpoint of its structure. As a result of such analysis, they found that the following matters are important for the metal complex organic substance to exhibit the ferromagnetic property.

(1) The metal complex organic substance is structured so that a heterocyle is bonded (for example, by means of coordination) to metal as an active site to exhibit the ferromagnetic property of metal complex organic molecules.

(2) Metals of a plurality of metal complex organic molecules are bonded to each other (by means of, for example, coordinate bonds), thereby forming a metal complex organic compound. The metals of the metal complex organic molecules can be bonded together via an electron donor (such as an oxygen atom) having an electron pair to be donated to the metals. For example, the oxygen atom derives from water. As the metal parts of the magnetic metal complex organic molecules which are respectively magnetic are bonded to each other (coordinate bonds) via the electron donor, the ferromagnetic property is exhibited. An example of the electron donor is not limited to a molecule including the oxygen atom as long as the electron donor has an electron pair that can be donated to the metal atoms of the metal complex molecules. For example, the electron donor may be an amine compound containing a nitrogen atom.

(3) There is a trade-off relationship between the stability and the ferromagnetic property of the crystal structure of the compound in which the plurality of metal complex organic molecules are bonded together via the electron donor. When the crystal structure of the metal complex organic compound is about to be stabilized, unpaired electron density of the metal complex compound decreases due to a superexchange interaction and the magnetic property of the crystal decreases. On the other hand, if an attempt is made to increase the magnetic property of the metal complex organic compound crystal, the stability of the metal complex organic compound crystal decreases.

As a bond angle formed by metal-electron donor-metal becomes closer to 90°, the unpaired electron density of the metal complex organic compound increases and a magnetization rate caused by the applied magnetic field increases, that is, the metal complex organic compound becomes more ferromagnetic; however, as the metal complex molecules become closer to each other, distortion of the molecule structure increases and a repulsive force between the molecules increases, thereby decreasing the stability of the crystal structure. On the other hand, as the bond angle formed by metal-electron donor-metal becomes closer to 180°, the crystal structure of the metal complex organic compound becomes stable; however, the superexchange interaction becomes predominant, the unpaired electron density decreases, and the magnetization rate decreases.

So, as a result of examination of the metal complex compound crystal by the inventors of the present application by means of X-ray analysis, it was found that regarding the metal complex organic compound having the structure in which the heterocycle molecule is bonded to the metal as an active site to exhibit the ferromagnetic property, the metals of two metal complex molecules are bonded together via the electron donor having the electron pair donated to the metals and, furthermore, the bond angle which forms metal-electron donor-metal bonding is within the range from 130° to 160°, so that the stability and the ferromagnetic property of the crystal structure of the metal complex compound are balanced at a higher dimension.

Therefore, the present disclosure is a magnetic substance containing a metal complex compound composed of a plurality of metal complex molecules in which a heterocycle is bonded to metal, wherein the metal of the metal complex molecule is bonded to the metal of another metal complex molecule via an electron donor and a metal-electron donor-metal bond angle is from 130° to 160°, preferably from 140° to 150°, more preferably from 144° to 147°, and most preferably 146.359°.

The heterocyle of the iron-salen complex molecule is a cyclic structure formed of two nitrogen atoms and two oxygen atoms which surround an iron (metal) atom in a flat form.

The plurality of metal complex molecules, particularly, two metal complex molecules, whose bond angle is formed within the above-mentioned range have high structural stability and high unpaired electron density and are thereby ferromagnetic. When the bond angle formed by the metal-electron donor-metal exceeds 160°, the structural stability of the crystal increases, but the unpaired electron density of the metal complex compound decreases and the magnetization rate decreases; and when the bond angle is less than 130°, the magnetization rate of the metal complex molecules increases, but the stability of the crystal decreases. Incidentally, in the latter case, the magnetization rate of the metal complex molecules increases, but the particle diameter decreases. As a result, the magnetization rate of the entire crystal decreases.

In order for the metal complex (organic) compound to sufficiently exhibit the magnetic property, it is preferable that regarding the metal complex compound having the structure in which the heterocycle is bonded to the metal as the active sit to exhibit the ferromagnetic property, the metals of the two metal complex molecules be bonded together via the electron donor and, furthermore, the bond angle which forms the metal-electron donor-metal bonding be from 130° to 160°, and the crystal particle diameter of the metal complex compound composed of the plurality of metal complex molecules should preferably be within the range from 200 nm to 700 nm, and more preferably within the range from 300 nm to 600 nm.

As a percentage of the metal complex compounds regarding which the metal-electron donor-metal bond angle is from 130° to 160° to the entire substance is higher, magnetic strength of the magnetic substance increases. The percentage of the metal complex compounds, which constitute the magnetic substance and regarding which the metal-electron donor-metal bond angle is within the range from 130° to 160°, to the entire substance should preferably be 50 wt % or more, more preferably 80 wt % or more.

In order to form the metal-electron donor-metal bond angle within the range from 130° to 160°, operation useful for crystallization of the metal complex compound is necessary. One example of such operation is optimization of the crystal particle diameter of the metal complex compound. If an average crystal particle diameter is less than 100 nm, distortion of the crystal structure increases and the stability decreases. On the other hand, if the average particle diameter exceeds 1 µm, the metal-electron donor-metal bond angle becomes closer to 180° and the magnetic property decreases. It is preferable that the crystal particle diameter of the metal complex compound be within the range from 200 nm to 700 nm inclusive, particularly within the range from 300 nm to 600 nm inclusive in order to form the metal-electron donor-metal bond angle within the range from 130° to 160°.

A preferred example of the metal complex is a metal-salen complex (Chem. 1 indicated below) and a preferred example of the electron donor having an electron donor group is oxygen that can donate electrons to iron. The magnetic substance composed of the metal complex organic compounds is formed by bonding of the metals of the two metal-salen complexes via oxygen as illustrated in Chem. 2 below. As the stability of the crystal structure and the unpaired electron density (magnetization rate) of the organic magnetic substance are balanced at a high dimension in the state where the metal-oxygen-metal bond angle is within the range from 130° to 160° and, furthermore, the distance between the metal and the oxygen is from 1.1 Å to 1.8 Å, the magnetic substance exhibits the stable ferromagnetic property. A coordinate bond is possible, other than a covalent bond, as bonding between the metal and the oxygen. An electron donating source of the electron donor may be oxygen of a water molecule. In this case, the metal parts of the metal complex organic molecules and the water molecule are bonded as follows.

M . . . O(H)$_2$ . . . M (the sign " . . . " represents a coordinate bond.)

Chem. 1 illustrated below represents a basic skeleton of the metal-salen complex molecule. M represents a center metal of the metal-salen complex. The center metal (M) is Fe, Cr, Mn, Co, Ni, Mo, Ru, Rh, Pd, W, Re, Os, Ir, Pt, Nd, Sm, Eu, or Gd. Chem. 2 illustrated below represents a basic skeleton of the metal-salen complex compound in which two metal-salen complex molecules described above are bonded together via the electron donor (O).

[Chem. 1]

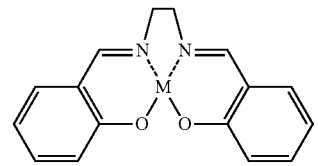

[Chem. 2]

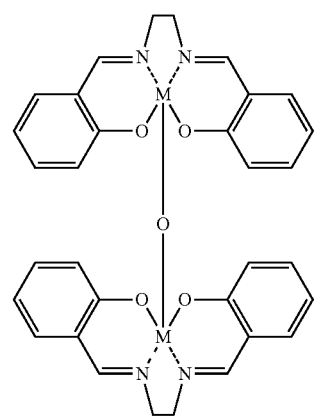

The metal complex molecule of the present disclosure includes derivatives of the metal-salen complex in Chem. 1 (not only molecules in which other functional groups are connected instead of hydrogens as side chains, but also a composite in which the metal-salen complex and another medicinal compound are bonded together (WO2010/058280) may be included). Incidentally, the magnetic substance of the present disclosure is used not only for magnetic drugs (such as anti-cancer drugs) mentioned earlier, but also for known usage, for example, as magnetic materials for electric and electronic parts, such as switching elements, or as contrast media for MRI.

Advantageous Effects of Disclosure

A magnetic substance capable of reliably exhibiting the ferromagnetic property can be provided according to the present disclosure.

MODE FOR CARRYING OUT THE DISCLOSURE

Manufacture of Metal-Salen Complex (Iron-Salen Complex)

Figure 1:
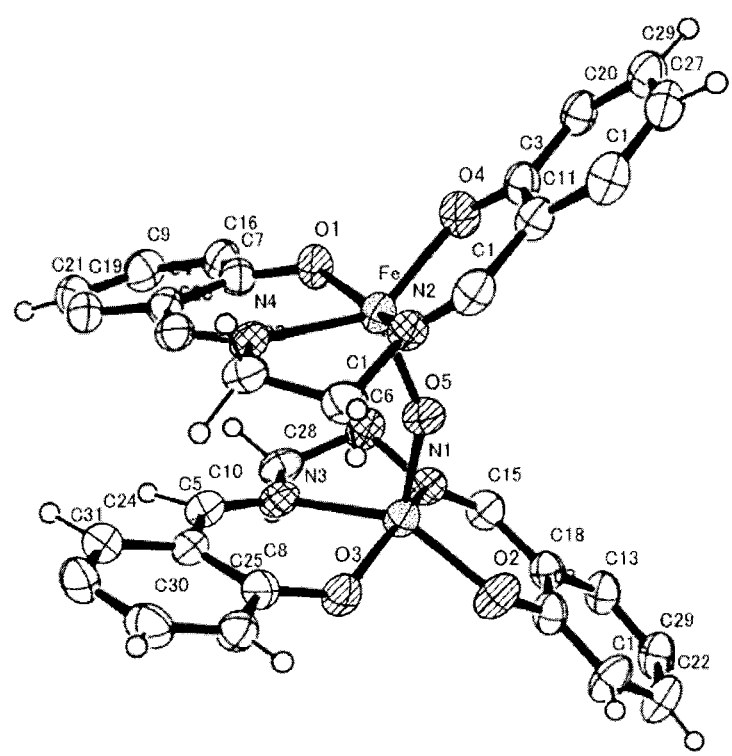
FIG. 1 is a perspective view of an iron-salen complex compound single crystal based on structure data of the iron-salen complex compound single crystal.
Figure 1:
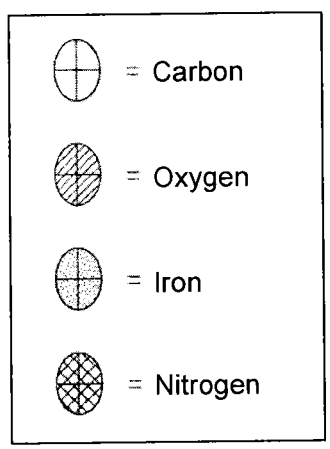

Iron-salen complex molecules were manufactured by the following process.

A salen ligand (N,N'-Bis(salicylidene)ethylenediamine) and its derivative are synthesized by a dehydration condensation reaction of the corresponding salicylaldehyde and a derivative of ethylene diamine. The obtained ligand is formed as a phenoxide ion derivative or is made to react with a metal ion under basic conditions, and then the metal-salen complex is formed. The detailed explanation will be given below.

Step 1:

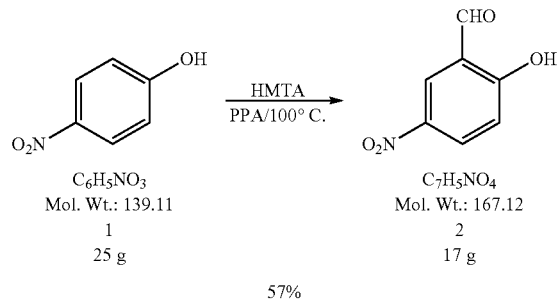

A mixture of 4-nitrophenol (25 g, 0.18 mol), hexamethylene tetramine (25 g, 0.18 mol), and polyphosphoric acid (200 ml) were stirred for one hour at the temperature of 100 degrees Celsius. Then, that mixture was introduced to 500 ml of ethyl acetate and 1 L of water and stirred until it completely dissolved. Furthermore, when 400 ml of ethyl acetate was added to that solution, the solution separated into two phases. Subsequently, an aqueous phase was removed from the solution; and the remaining compound was washed twice with a basic solvent and dried over anhydrous $MgSO_4$. As a result, 17 g of Compound 2 (57% yield) was synthesized.

Step 2:

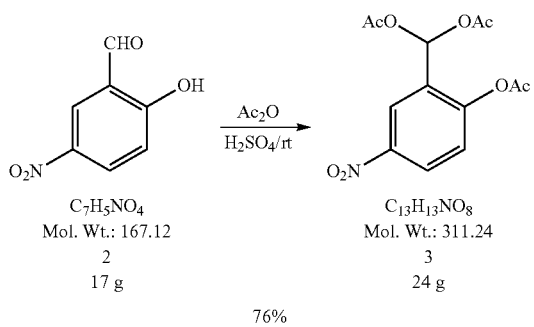 [SMILES: "Ac2O" ; O=Cc1cc([N+](=O)[O-])ccc1O ; CC(=O)Oc1ccc([N+](=O)[O-])cc1C(OC(C)=O)OC(C)=O]

Compound 2 (17 g, 0.10 mol), acetic anhydride (200 ml) and $H_2SO_4$ (minimal) were stirred for one hour at room temperature. The resulting solution was mixed for 0.5 hour in iced water (2 L) to bring about hydrolysis. The resulting solution was filtered and dried in air, thereby obtaining white powder. The powder was recrystallized, using a solvent containing ethyl acetate. As a result, 24 g of Compound 3 (76% yield) was obtained in the form of white crystals.

Step 3:

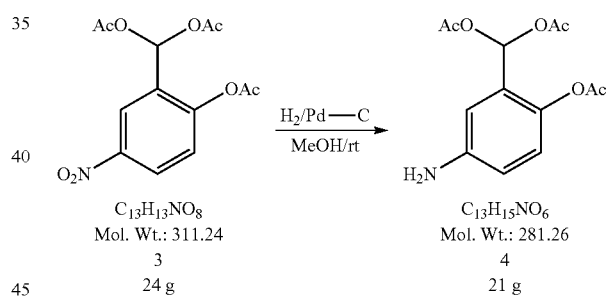

A mixture of carbon (2.4 g) supporting 10% palladium with Compound 3 (24 g, 77 mmol) and methanol (500 ml) was reduced over night in a 1.5 atm hydrogen reducing atmosphere. After the reduction was completed, the product was filtered, thereby allowing Compound 4 (21 g) in the form of brown oil to be synthesized.

Step 4, 5:

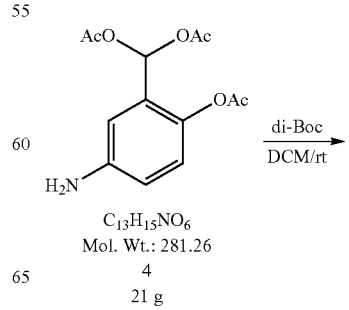

-continued

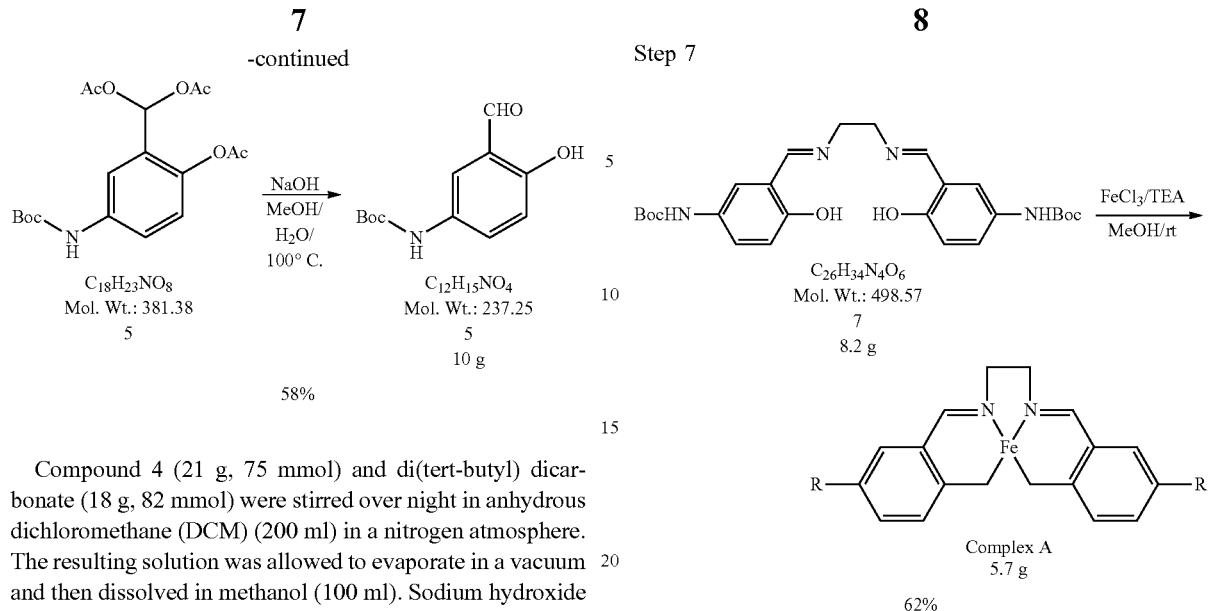

Compound 4 (21 g, 75 mmol) and di(tert-butyl) dicarbonate (18 g, 82 mmol) were stirred over night in anhydrous dichloromethane (DCM) (200 ml) in a nitrogen atmosphere. The resulting solution was allowed to evaporate in a vacuum and then dissolved in methanol (100 ml). Sodium hydroxide (15 g, 374 mmol) and water (50 ml) were then added and the solution was brought to reflux for 5 hours. The solution was then cooled, filtered, washed with water, and allowed to dry in a vacuum, thereby obtaining a brown compound. The resulting compound was processed twice by flash chromatography using silica gel, thereby obtaining 10 g of Compound 6 (58% yield).

Step 6:

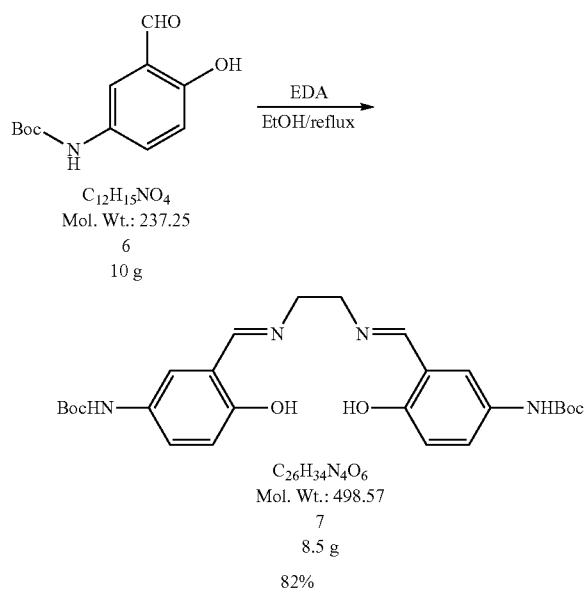

Compound 6 (10 g, 42 mmol) was introduced into 400 ml of anhydrous ethanol, the mixture was brought to reflux while heated, and several drops of ethylene diamine (1.3 g, 21 mmol) were added into 20 ml of anhydrous ethanol while stirred for 0.5 hour. The mixture was introduced into a container of ice, where it was cooled and mixed for 15 minutes. It was then washed with 200 ml of ethanol, filtered, and dried in a vacuum, thereby obtaining 8.5 g of Compound 7 (82% yield).

Step 7

Compound 7 (8.2 g, 16 mmol) and triethylamine (22 ml, 160 mmol) were introduced into dehydrated methanol (50 ml) and the obtained solution was mixed with a solution of $FeCl_3$ (2.7 g, 16 mmol) added in 10 ml methanol in a nitrogen atmosphere. The ingredients were mixed for one hour in the nitrogen atmosphere at the room temperature, thereby obtaining a brown compound. The obtained compound was heated to 80 degrees Celsius and then a quenching treatment by water cooling was applied to the compound to make the temperature of the compound become room temperature; and after that, the compound was filtered and the filtered crystals were then dried in a vacuum. The obtained crystals were washed twice with 400 ml of dichloromethane and a saline solution (tetrahydrofuran), respectively, and then filtered with a 0.22 μm filter, dried in $Na_2SO_4$, and further dried in vacuum, thereby obtaining complex A (iron-salen complex compound [in which all R's are H]). It is desirable that supersonic waves should be applied to a solution of the metal complex for a certain period of time, for example, about one hour in order to have crystal grains arranged within a proper range, that is, to make the crystal grains in an even crystal particle diameter (frequency: 2 kHz; and device name: SONIFIER 250 (BRANSON)).

The resulting compound was recrystallized in a solution of diethyl ether and paraffin, and assay of the crystals by high-speed liquid chromatography revealed that 5.7 g of complex A (iron-salen complex compound of Chem. 1, R=H) of purity of 95% or higher was obtained (62% yield). Recrystallization was conducted under quenching conditions in the same manner as described above. Incidentally, the reaction of Step 7 may be caused while heated. In this case, it is unnecessary to heat the obtained compound. If a metal complex other than the iron-salen complex is to be used, a chloride $MCl_3$ of the metal other than iron may be used instead of $FeCl_3$.

A plurality of iron-salen complexes (5-6 examples) were obtained by repeatedly executing the above-mentioned steps. Crystals of the highest magnetic property were extracted from each iron-salen complex. A measured value of saturation magnetization of the crystals having the highest magnetic property was 1.25 emu/g. The measurement was conducted based on a magnetic property evaluation device MPMS7 manufactured by Kantum. The measured value of the crystals having the lowest magnetic property among those complexes was 0.02 (emu/g).

Next, the particle diameter of a single crystal of the salen complex having the highest ferromagnetic property was measured by using an electron microscope. A used device, conditions, and so on are as follows.
Device: transmission electron microscope (H-7100FA manufactured by Hitachi)
Conditions: acceleration voltage 100 kV
Sample adjustment: dispersion method (after the salen complex was ground with a mortar, pure water was added to the ground salen complex, which was then dispersed in a grid by TEM)
Grain size distribution measurement software: Image-Pro plus (Media cybermetrics, MD, U.S.A.)
Measured target: traced images of the iron-salen complex in TEM photographs
Number of samples: 140

As a result, an average particle diameter was 450 nm.

Next, the crystal structure of the single crystal of the iron-salen complex having the highest magnetic property was analyzed. The crystal structure was analyzed by using a SPring-8 microbeam line BL32XU. Measurement conditions are as follows.
Wavelength (A): 0.7 Å
Beam size: 1.0×1.5 (W×V) [um^2]
Photon flux: 3.0E10 [phs/sec.]
Total oscillation: 90 deg×4 sets
Oscillation: width 5 deg/frame Reflected X-rays from the iron-salen complex were photographed with a Laue camera, thereby obtaining Laue spots. Factors of the crystal structure were found by executing respective processing for indexing of these Laue spots, integration of strength, normalization of wavelengths, and scaling. Such processing was executed by using software SHELXS (product name) for analyzing the Laue spots and determining data of the crystal structure. As a result, the following crystal structure data were obtained.

Incidentally, the crystal data explained below are based on the format of a crystal structure database of Cambridge University in the U.K. and are registered with the registration number CCDC-906837 in the university's crystal database.

```
_chemical_name_common
"N,N'-bis(salicylidene)ethylenediamine iron(II)"
_chemical_melting_point             ?
_chemical_formula_moiety            'C16 H14 Fe N2 O2'
_chemical_formula_sum               'C16 H14 Fe N2 O2'
_chemical_formula_weight            322.14
loop_
_atom_type_symbol
_atom_type_description
_atom_type_scat_dispersion_real
_atom_type_scat_dispersion_imag
_atom_type_scat_source
C C 0.0033 0.0016 'International Tables Vol C Tables 4.2.6.8 and 6.1.1.4'
H H 0.0000 0.0000 'International Tables Vol C Tables 4.2.6.8 and 6.1.1.4'
Fe Fe 0.3463 0.8444 'International Tables Vol C Tables 4.2.6.8 and 6.1.1.4'
N N 0.0061 0.0033 'International Tables Vol C Tables 4.2.6.8 and 6.1.1.4'
O O 0.0106 0.0060 'International Tables Vol C Tables 4.2.6.8 and 6.1.1.4'
_symmetry_cell_setting              triclinic
_symmetry_space_group_name_H-M      'P-1'
loop_
_symmetry_equiv_pos_as_xyz
'x, y, z'
'-x, -y, -z'
_cell_length_a                      10.748(10)
_cell_length_b                      10.76(2)
_cell_length_c                      13.768(10)
_cell_angle_alpha                   66.49(4)
_cell_angle_beta                    81.10(2)
_cell_angle_gamma                   73.12(5)
_cell_volume                        1396(3)
_cell_formula_units_Z               2
_cell_measurement_temperature       100(2)
_cell_measurement_reflns_used       ?
_cell_measurement_theta_min         ?
_cell_measurement_theta_max         ?
_exptl_crystal_description          needle
_exptl_crystal_colour               Brown
_exptl_crystal_size_max             0.04
_exptl_crystal_size_mid             0.005
_exptl_crystal_size_min             0.005
_exptl_crystal_density_meas         ?
_exptl_crystal_density_diffrn       0.767
_exptl_crystal_density_method       'not measured'
_exptl_crystal_F_000                332
_exptl_absorpt_coefficient_mu       0.543
_exptl_absorpt_correction_type      ?
_exptl_absorpt_correction_T_min     ?
_exptl_absorpt_correction_T_max     ?
_exptl_absorpt_process_details      ?
_exptl_special_details
_diffrn_ambient_temperature         100(2)
_diffrn_radiation_wavelength        0.6888
_diffrn_radiation_type              'synchrotron radiation'
```

-continued

| | |
|---|---|
| _diffrn_radiation_source | 'synchrotron radiation' |
| _diffrn_radiation_monochromator | silicon |
| _diffrn_measurement_device_type | 'KOHZU KSU' |
| _diffrn_measurement_method | ? |
| _diffrn_detector_area_resol_mean | ? |
| _diffrn_standards_number | ? |
| _diffrn_standards_interval_count | ? |
| _diffrn_standards_interval_time | ? |
| _diffrn_standards_decay_% | ? |
| _diffrn_reflns_number | 4022 |
| _diffrn_reflns_av_R_equivalents | 0.0000 |
| _diffrn_reflns_av_sigmaI/netI | 0.0525 |
| _diffrn_reflns_limit_h_min | 0 |
| _diffrn_reflns_limit_h_max | 12 |
| _diffrn_reflns_limit_k_min | −11 |
| _diffrn_reflns_limit_k_max | 12 |
| _diffrn_reflns_limit_l_min | −15 |
| _diffrn_reflns_limit_l_max | 15 |
| _diffrn_reflns_theta_min | 1.59 |
| _diffrn_reflns_theta_max | 23.76 |
| _reflns_number_total | 4022 |
| _reflns_number_gt | 3236 |
| _reflns_threshold_expression | >2sigma(I) |
| _computing_data_collection | 'DENZO/SCALEPACK (Otwinowski, 1997)' |
| _computing_cell_refinement | 'DENZO/SCALEPACK (Otwinowski, 1997)' |
| _computing_data_reduction | 'DENZO/SCALEPACK (Otwinowski, 1997)' |
| _computing_structure_solution | 'SHELXS-97 (Sheldrick, 1990)' |
| _computing_structure_refinement | 'SHELXL-97 (Sheldrick, 1997)' |
| _computing_molecular_graphics | ? |
| _computing_publication_material | ? |
| _refine_special_details | |

Refinement of $F^2$ against ALL reflections. The weighted R-factor wR and goodness of fit S are based on $F^2$, conventional R-factors R are based on F, with F set to zero for negative $F^2$. The threshold expression of $F^2 > 2sigma(F^2)$ is used only for calculating R-factors(gt) etc. and is not relevant to the choice of reflections for refinement. R-factors based on $F^2$ are statistically about twice as large as those based on F, and R-factors based on ALL data will be even larger.

| | |
|---|---|
| _refine_ls_structure_factor_coef | Fsqd |
| _refine_ls_matrix_type | full |
| _refine_ls_weighting_scheme | calc |
| _refine_ls_weighting_details | |

'calc w=1/[$\Ys^2(Fo^2)+(0.1000P)^2+0.0000P$] where P=($Fo^2+2Fc^2$)/3'

| | |
|---|---|
| _atom_sites_solution_primary | direct |
| _atom_sites_solution_secondary | difmap |
| _atom_sites_solution_hydrogens | geom |
| _refine_ls_hydrogen_treatment | mixed |
| _refine_ls_extinction_method | none |
| _refine_ls_extinction_coef | ? |
| _refine_ls_number_reflns | 4022 |
| _refine_ls_number_parameters | 429 |
| _refine_ls_number_restraints | 0 |
| _refine_ls_R_factor_all | 0.0813 |
| _refine_ls_R_factor_gt | 0.0633 |
| _refine_ls_wR_factor_ref | 0.1818 |
| _refine_ls_wR_factor_gt | 0.1627 |
| _refine_ls_goodness_of_fit_ref | 1.335 |
| _refine_ls_restrained_S_all | 1.385 |
| _refine_ls_shift/su_max | 2.089 |
| _refine_ls_shift/su_mean | 0.005 | loop_
_atom_site_label
_atom_site_type_symbol
_atom_site_fract_x
_atom_site_fract_y
_atom_site_fract_z
_atom_site_U_iso_or_equiv
_atom_site_adp_type
_atom_site_occupancy
_atom_site_symmetry_multiplicity
_atom_site_calc_flag
_atom_site_refinement_flags
_atom_site_disorder_assembly
_atom_site_disorder_group
Fe1 Fe 0.82263(7) 0.54475(7) 0.29332(5) 0.0284(3) Uani 1 1 d . . .
Fe2 Fe 0.86409(7) 0.78733(7) 0.04555(5) 0.0287(3) Uani 1 1 d . . .
O1 O 0.6682(3) 0.4905(4) 0.3660(3) 0.0345(9) Uani 1 1 d . . .
O2 O 1.0276(3) 0.6928(4) −0.0033(3) 0.0345(9) Uani 1 1 d . . .
O3 O 0.7861(4) 0.8437(4) −0.0868(3) 0.0423(10) Uani 1 1 d . . .

-continued

```
O4 O 0.8173(3) 0.6645(4) 0.3697(3) 0.0330(8) Uani 1 1 d . . .
O5 O 0.8022(4) 0.6599(4) 0.1559(3) 0.0356(9) Uani 1 1 d . . .
N1 N 0.9801(5) 0.8557(5) 0.1171(3) 0.0344(11) Uani 1 1 d . . .
N2 N 1.0230(4) 0.4703(5) 0.3189(3) 0.0298(10) Uani 1 1 d . . .
N3 N 0.7407(5) 0.9733(5) 0.0556(3) 0.0342(10) Uani 1 1 d . . .
N4 N 0.8731(4) 0.3571(4) 0.2668(3) 0.0311(10) Uani 1 1 d . . .
C1 C 1.0922(6) 0.3505(6) 0.2884(4) 0.0385(13) Uani 1 1 d . . .
H11 H 1.1126 0.2657 0.3512 0.031(14) Uiso 1 1 calc R . .
H32 H 1.1731 0.3664 0.2494 0.06(2) Uiso 1 1 calc R . .
C2 C 1.1405(5) 0.6356(6) 0.0413(4) 0.0300(11) Uani 1 1 d . . .
C3 C 0.9080(5) 0.7056(5) 0.3931(4) 0.0282(11) Uani 1 1 d . . .
C4 C 0.6741(5) 0.2858(6) 0.3342(4) 0.0328(12) Uani 1 1 d . . .
C5 C 0.6228(5) 1.0562(6) −0.1040(4) 0.0335(12) Uani 1 1 d . . .
C6 C 0.9110(6) 0.9775(6) 0.1464(4) 0.0346(13) Uani 1 1 d . . .
H23 H 0.9328 1.0618 0.0948 0.018(12) Uiso 1 1 calc R . .
H24 H 0.9369 0.9631 0.2154 0.015(11) Uiso 1 1 calc R . .
C7 C 0.6128(5) 0.3930(5) 0.3741(4) 0.0290(11) Uani 1 1 d . . .
C8 C 0.6932(6) 0.9498(6) −0.1402(4) 0.0376(13) Uani 1 1 d . . .
C9 C 0.4285(5) 0.2892(6) 0.4384(4) 0.0339(12) Uani 1 1 d . . .
H3 H 0.3476 0.2901 0.4743 0.025(13) Uiso 1 1 calc R . .
C10 C 0.6484(5) 1.0624(6) −0.0049(4) 0.0352(13) Uani 1 1 d . . .
H28 H 0.6626 1.1542 −0.0229 0.36(12) Uiso 1 1 calc R . .
H34 H 0.5683 1.0601 0.0385 1.2(7) Uiso 1 1 calc R . .
C11 C 1.0423(5) 0.6352(6) 0.3917(4) 0.0315(12) Uani 1 1 d . . .
C12 C 1.2293(6) 0.5244(6) 0.0164(4) 0.0383(13) Uani 1 1 d . . .
H16 H 1.211(6) 0.488(7) −0.026(4) 0.047(18) Uiso 1 1 d . . .
C13 C 1.3022(6) 0.6129(6) 0.1578(4) 0.0413(14) Uani 1 1 d . . .
H22 H 1.3277 0.6428 0.2046 0.036(15) Uiso 1 1 calc R . .
C14 C 1.0911(5) 0.5180(6) 0.3600(4) 0.0351(13) Uani 1 1 d . . .
H26 H 1.1632 0.5386 0.3096 0.26(8) Uiso 1 1 calc R . .
H33 H 1.1287 0.4397 0.4222 2.0(17) Uiso 1 1 calc R . .
C15 C 1.0993(6) 0.7947(6) 0.1413(4) 0.0363(13) Uani 1 1 d . . .
H12 H 1.0999 0.7617 0.2180 0.5(2) Uiso 1 1 calc R . .
H35 H 1.1456 0.8678 0.1135 0.33(11) Uiso 1 1 calc R . .
C16 C 0.4902(5) 0.3919(6) 0.4257(4) 0.0317(12) Uani 1 1 d . . .
H6 H 0.4491 0.4616 0.4522 0.034(14) Uiso 1 1 calc R . .
C17 C 1.1330(6) 0.6868(7) 0.4192(4) 0.0396(14) Uani 1 1 d . . .
C18 C 1.1791(5) 0.6805(6) 0.1127(4) 0.0346(12) Uani 1 1 d . . .
C19 C 0.6067(6) 0.1839(6) 0.3463(4) 0.0373(13) Uani 1 1 d . . .
H7 H 0.648(5) 0.108(6) 0.321(4) 0.037(15) Uiso 1 1 d . . .
C20 C 0.8734(6) 0.8237(6) 0.4208(4) 0.0343(12) Uani 1 1 d . . .
H2 H 0.7860 0.8703 0.4233 0.034(15) Uiso 1 1 calc R . .
C21 C 1.0040(5) 0.3350(5) 0.2190(4) 0.0385(13) Uani 1 1 d . . .
H9 H 1.0063 0.4037 0.1474 0.043(16) Uiso 1 1 calc R . .
H10 H 1.0325 0.2422 0.2163 0.019(12) Uiso 1 1 calc R . .
C22 C 1.3463(6) 0.4595(6) 0.0623(4) 0.0432(14) Uani 1 1 d . . .
H29 H 1.4017 0.3850 0.0466 0.09(3) Uiso 1 1 calc R . .
C23 C 0.9651(6) 0.8725(7) 0.4443(4) 0.0404(14) Uani 1 1 d . . .
H31 H 0.9392 0.9528 0.4602 0.06(2) Uiso 1 1 calc R . .
C24 C 0.5256(6) 1.1664(6) −0.1657(5) 0.0409(13) Uani 1 1 d . . .
H27 H 0.4762 1.2342 −0.1398 0.07(2) Uiso 1 1 calc R . .
C25 C 0.6663(6) 0.9607(6) −0.2398(5) 0.0464(15) Uani 1 1 d . . .
H18 H 0.7122 0.8914 −0.2654 0.07(2) Uiso 1 1 calc R . .
C26 C 0.8028(6) 0.2718(6) 0.2828(4) 0.0366(13) Uani 1 1 d . . .
H8 H 0.8540 0.1792 0.3234 0.33(11) Uiso 1 1 calc R . .
H25 H 0.7933 0.2715 0.2139 1.0(5) Uiso 1 1 calc R . .
C27 C 1.0956(6) 0.8031(7) 0.4446(5) 0.0491(16) Uani 1 1 d . . .
H21 H 1.1572 0.8354 0.4619 0.08(2) Uiso 1 1 calc R . .
C28 C 0.7665(6) 0.9929(6) 0.1494(4) 0.0397(14) Uani 1 1 d . . .
H5 H 0.7402 0.9230 0.2136 0.043(16) Uiso 1 1 calc R . .
H19 H 0.7185 1.0850 0.1480 0.06(2) Uiso 1 1 calc R . .
C29 C 1.3838(6) 0.5053(7) 0.1341(5) 0.0470(15) Uani 1 1 d . . .
H13 H 1.4642 0.4617 0.1649 0.055(19) Uiso 1 1 calc R . .
C30 C 0.5738(6) 1.0711(7) −0.3009(5) 0.0495(16) Uani 1 1 d . . .
H14 H 0.5586 1.0761 −0.3672 0.027(13) Uiso 1 1 calc R . .
C31 C 0.5029(6) 1.1751(6) −0.2646(5) 0.0442(14) Uani 1 1 d . . .
H15 H 0.4405 1.2500 −0.3063 0.08(2) Uiso 1 1 calc R . .
C32 C 0.4856(6) 0.1857(6) 0.3986(4) 0.0418(14) Uani 1 1 d . . .
H20 H 0.4432 0.1179 0.4067 0.049(18) Uiso 1 1 calc R . .
H4 H 1.229(5) 0.634(5) 0.421(4) 0.020(12) Uiso 1 1 d . . .
loop_
_atom_site_aniso_label
_atom_site_aniso_U_11
_atom_site_aniso_U_22
_atom_site_aniso_U_33
_atom_site_aniso_U_23
_atom_site_aniso_U_13
_atom_site_aniso_U_12
Fe1 0.0268(4) 0.0298(4) 0.0271(4) −0.0124(3) −0.0010(3) −0.0027(3)
```

-continued

```
Fe2 0.0323(5) 0.0291(4) 0.0224(4) −0.0105(3) −0.0043(3) −0.0018(3)
O1 0.035(2) 0.036(2) 0.035(2) −0.0189(17) 0.0053(17) −0.0085(17)
O2 0.035(2) 0.037(2) 0.0305(19) −0.0166(16) −0.0056(16) 0.0004(17)
O3 0.053(3) 0.037(2) 0.035(2) −0.0213(17) −0.0178(18) 0.0126(18)
O4 0.031(2) 0.040(2) 0.0306(19) −0.0168(16) 0.0026(16) −0.0092(16)
O5 0.036(2) 0.039(2) 0.0285(19) −0.0118(16) −0.0045(16) −0.0041(16)
N1 0.046(3) 0.037(2) 0.017(2) −0.0089(19) −0.001(2) −0.009(2)
N2 0.030(2) 0.035(2) 0.020(2) −0.0103(18) −0.0017(18) −0.0010(18)
N3 0.039(3) 0.033(2) 0.028(2) −0.0129(19) 0.001(2) −0.004(2)
N4 0.034(3) 0.033(2) 0.023(2) −0.0122(18) −0.0033(18) 0.000(2)
C1 0.037(3) 0.041(3) 0.031(3) −0.013(2) 0.001(2) −0.002(2)
C2 0.028(3) 0.038(3) 0.022(2) −0.009(2) −0.001(2) −0.008(2)
C3 0.030(3) 0.034(3) 0.018(2) −0.007(2) −0.005(2) −0.007(2)
C4 0.036(3) 0.036(3) 0.025(3) −0.014(2) −0.007(2) −0.001(2)
C5 0.031(3) 0.037(3) 0.030(3) −0.014(2) 0.003(2) −0.005(2)
C6 0.052(4) 0.033(3) 0.022(3) −0.012(2) −0.004(2) −0.01.3(3)
C7 0.028(3) 0.032(3) 0.028(3) −0.013(2) −0.013(2) −0.003(2)
C8 0.040(3) 0.035(3) 0.034(3) −0.014(2) −0.011(2) 0.001(2)
C9 0.034(3) 0.040(3) 0.027(3) −0.011(2) −0.006(2) −0.008(2)
C10 0.037(3) 0.033(3) 0.031(3) −0.012(2) 0.007(2) −0.007(2)
C11 0.030(3) 0.042(3) 0.023(2) −0.009(2) −0.004(2) −0.012(2)
C12 0.039(3) 0.045(3) 0.030(3) −0.017(3) 0.003(2) −0.007(3)
C13 0.043(3) 0.054(4) 0.025(3) −0.009(3) 0.000(3) −0.018(3)
C14 0.036(3) 0.044(3) 0.017(2) −0.008(2) 0.003(2) −0.006(2)
C15 0.040(3) 0.042(3) 0.021(2) −0.002(2) −0.001(2) −0.014(3)
C16 0.035(3) 0.034(3) 0.032(3) −0.020(2) −0.002(2) −0.005(2)
C17 0.030(3) 0.060(4) 0.026(3) −0.014(3) −0.005(2) −0.009(3)
C18 0.033(3) 0.039(3) 0.028(3) −0.009(2) 0.003(2) −0.011(2)
C19 0.049(4) 0.034(3) 0.033(3) −0.016(2) −0.009(3) −0.008(3)
C20 0.039(3) 0.041(3) 0.024(3) −0.013(2) −0.001(2) −0.011(3)
C21 0.036(3) 0.043(3) 0.027(3) −0.015(2) 0.004(2) 0.003(2)
C22 0.033(3) 0.044(3) 0.040(3) −0.012(3) 0.001(3) 0.002(3)
C23 0.052(4) 0.049(3) 0.028(3) −0.015(3) −0.002(3) −0.022(3)
C24 0.034(3) 0.034(3) 0.053(3) −0.019(3) −0.004(3) −0.001(2)
C25 0.055(4) 0.038(3) 0.043(3) −0.024(3) −0.016(3) 0.011(3)
C26 0.046(3) 0.031(3) 0.031(3) −0.014(2) −0.005(3) −0.003(3)
C27 0.050(4) 0.072(4) 0.039(3) −0.023(3) −0.001(3) −0.033(4)
C28 0.049(4) 0.040(3) 0.027(3) −0.016(2) 0.004(2) −0.005(3)
C29 0.031(3) 0.058(4) 0.043(3) −0.012(3) −0.004(3) −0.005(3)
C30 0.055(4) 0.052(4) 0.042(3) −0.023(3) −0.019(3) 0.001(3)
C31 0.039(3) 0.035(3) 0.052(4) −0.011(3) −0.019(3) 0.002(3)
C32 0.050(4) 0.042(3) 0.036(3) −0.009(3) −0.008(3) −0.019(3)
_geom_special_details
```

All esds (except the esd in the dihedral angle between two l.s. planes) are estimated using the full covariance matrix. The cell esds are taken into account individually in the estimation of esds in distances, angles and torsion angles; correlations between esds in cell parameters are only used when they are defined by crystal symmetry. An approximate (isotropic) treatment of cell esds is used for estimating esds involving l.s. planes.

```
loop_
_geom_bond_atom_site_label_1
_geom_bond_atom_site_label_2
_geom_bond_distance
_geom_bond_site_symmetry_2
_geom_bond_publ_flag
Fe1 O5 1.806(4) . ?
Fe1 O1 1.918(4) . ?
Fe1 O4 1.947(4) . ?
Fe1 N4 2.096(6) . ?
Fe1 N2 2.101(5) . ?
Fe2 O5 1.785(4) . ?
Fe2 O3 1.921(4) . ?
Fe2 O2 1.929(4) . ?
Fe2 N3 2.098(6) . ?
Fe2 N1 2.134(5) . ?
O1 C7 1.310(7) . ?
O2 C2 1.313(6) . ?
O3 C8 1.317(6) . ?
O4 C3 1.307(6) . ?
N1 C15 1.287(7) . ?
```

-continued

```
N1 C6 1.482(7) . ?
N2 C14 1.302(7) . ?
N2 C1 1.473(7) . ?
N3 C10 1.290(7) . ?
N3 C28 1.468(7) . ?
N4 C26 1.286(7) . ?
N4 C21 1.453(7) . ?
C1 C21 1.529(8) . ?
C2 C12 1.423(8) . ?
C2 C18 1.412(8) . ?
C3 C20 1.403(8) . ?
C3 C11 1.424(8) . ?
C4 C19 1.425(8) . ?
C4 C7 1.421(8) . ?
C4 C26 1.449(8) . ?
C5 C8 1.403(8) . ?
C5 C24 1.404(8) . ?
C5 C10 1.463(8) . ?
C6 C28 1.509(8) . ?
C7 C16 1.398(7) . ?
C8 C25 1.398(8) . ?
C9 C16 1.389(8) . ?
C9 C32 1.380(8) . ?
C11 C17 1.413(8) . ?
C11 C14 1.428(8) . ?
C12 C22 1.361(8) . ?
C13 C29 1.356(9) . ?
C13 C18 1.414(8) . ?
C15 C18 1.439(8) . ?
C17 C27 1.365(9) . ?
C19 C32 1.386(9) . ?
```

```
C20 C23 1.373(8) . ?
C22 C29 1.417(9) . ?
C23 C27 1.385(9) . ?
C24 C31 1.383(9) . ?
C25 C30 1.372(8) . ?
C30 C31 1.384(9) . ?
loop_
_geom_angle_atom_site_label_1
_geom_angle_atom_site_label_2
_geom_angle_atom_site_label_3
_geom_angle
_geom_angle_site_symmetry_1
_geom_angle_site_symmetry_3
_geom_angle_publ_flag
O5 Fe1 O1 114.25(17) . . ?
O5 Fe1 O4 105.7(2) . . ?
O1 Fe1 O4 93.46(16) . . ?
O5 Fe1 N4 96.22(19) . . ?
O1 Fe1 N4 86.43(18) . . ?
O4 Fe1 N4 155.83(16) . . ?
O5 Fe1 N2 107.96(17) . . ?
O1 Fe1 N2 135.90(17) . . ?
O4 Fe1 N2 86.84(17) . . ?
N4 Fe1 N2 76.74(18) . . ?
O5 Fe2 O3 115.43(18) . . ?
O5 Fe2 O2 108.05(19) . . ?
O3 Fe2 O2 92.15(16) . . ?
O5 Fe2 N3 100.7(2) . . ?
O3 Fe2 N3 85.88(17) . . ?
O2 Fe2 N3 148.89(18) . . ?
O5 Fe2 N1 103.36(18) . . ?
O3 Fe2 N1 139.76(18) . . ?
O2 Fe2 N1 85.45(19) . . ?
N3 Fe2 N1 76.5(2) . . ?
C7 O1 Fe1 134.2(3) . . ?
C2 O2 Fe2 130.0(3) . . ?
C8 O3 Fe2 134.9(3) . . ?
C3 O4 Fe1 132.4(3) . . ?
Fe2 O5 Fe1 145.3(2) . . ?
C15 N1 C6 119.4(5) . . ?
C15 N1 Fe2 125.1(4) . . ?
C6 N1 Fe2 115.3(3) . . ?
C14 N2 C1 117.2(5) . . ?
C14 N2 Fe1 126.7(4) . . ?
C1 N2 Fe1 116.1(3) . . ?
C10 N3 C28 119.8(5) . . ?
C10 N3 Fe2 129.3(4) . . ?
C28 N3 Fe2 110.8(3) . . ?
C26 N4 C21 121.2(5) . . ?
C26 N4 Fe1 128.5(4) . . ?
C21 N4 Fe1 110.2(4) . . ?
N2 C1 C21 108.1(4) . . ?
O2 C2 C12 119.2(5) . . ?
O2 C2 C18 123.0(5) . . ?
C12 C2 C18 117.9(5) . . ?
O4 C3 C20 119.5(5) . . ?
O4 C3 C11 122.7(5) . . ?
C20 C3 C11 117.8(5) . . ?
C19 C4 C7 118.7(5) . . ?
C19 C4 C26 117.3(5) . . ?
C7 C4 C26 124.0(5) . . ?
C8 C5 C24 120.0(5) . . ?
C8 C5 C10 123.2(5) . . ?
C24 C5 C10 116.8(5) . . ?
N1 C6 C28 108.4(4) . . ?
O1 C7 C16 119.2(5) . . ?
O1 C7 C4 122.4(5) . . ?
C16 C7 C4 118.5(5) . . ?
O3 C8 C5 123.3(5) . . ?
O3 C8 C25 118.8(5) . . ?
C5 C8 C25 117.9(5) . . ?
C16 C9 C32 120.8(5) . . ?
N3 C10 C5 123.2(5) . . ?
C17 C11 C3 118.5(5) . . ?
C17 C11 C14 118.1(5) . . ?
C3 C11 C14 123.4(5) . . ?
C22 C12 C2 121.5(6) . . ?
C29 C13 C18 121.3(6) . . ?
N2 C14 C11 125.4(5) . . ?
N1 C15 C18 124.9(5) . . ?
C9 C16 C7 121.4(5) . . ?
C27 C17 C11 122.0(6) . . ?
C13 C18 C2 119.5(5) . . ?
C13 C18 C15 117.6(5) . . ?
C2 C18 C15 122.9(5) . . ?
C32 C19 C4 121.3(6) . . ?
C23 C20 C3 121.8(5) . . ?
N4 C21 C1 106.9(4) . . ?
C12 C22 C29 120.1(6) . . ?
C20 C23 C27 120.6(6) . . ?
C31 C24 C5 120.6(5) . . ?
C30 C25 C8 121.7(6) . . ?
N4 C26 C4 123.3(5) . . ?
C17 C27 C23 119.3(5) . . ?
N3 C28 C6 106.9(4) . . ?
C13 C29 C22 119.8(6) . . ?
C25 C30 C31 120.5(6) . . ?
C24 C31 C30 119.3(5) . . ?
C19 C32 C9 119.3(5) . . ?
_diffrn_measured_fraction_theta_max    0.901
_diffrn_reflns_theta_full              23.76
_diffrn_measured_fraction_theta_full   0.901
_refine_diff_density_max               0.625
_refine_diff_density_min              −0.670
_refine_diff_density_rms               0.111
```

The crystal structure was analyzed based on these crystal structure data. The software SHELXS for creating a three-dimensional structure of crystals from crystal data was used for this analysis. FIG. 1 was drawn based on this three-dimensional structure and is a perspective view of an iron-salen complex organic compound in which two molecules of the iron-salen complex are bound together via water intercalated between them. A bond angle formed by Fe—O—Fe was 146.359. Furthermore, representative structure data of this crystal are as follows.

Lattice Constants
a=10.748 Angstrom
b=10.759 Angstrom
c=13.768 Angstrom
α=66.492°
β=81.096°
γ=73.125°
Space Group
P-1

Figure 3:
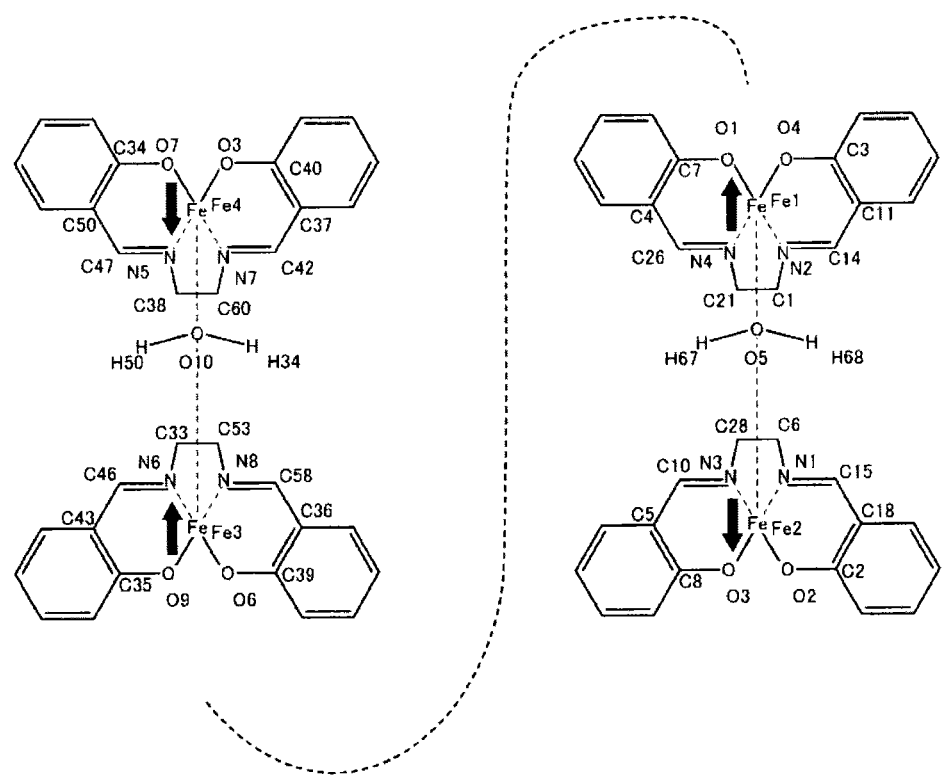
FIG. 3 is a molecular formula representing an iron atom spin orientation of a diamagnetic substance 1 (iron-salen complex compound)
Figure 4:
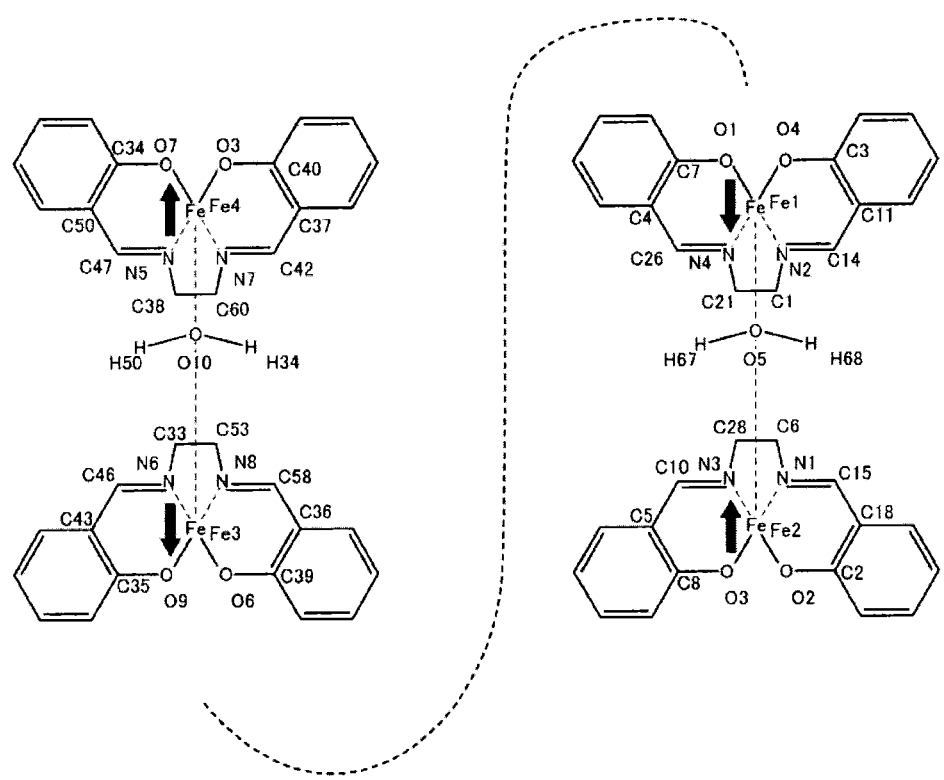
FIG. 4 is a molecular formula representing an iron atom spin orientation of a diamagnetic substance 2 (iron-salen complex compound).

It was verified that this crystal structure was actually stable. This verification was conducted by using Accelrys' software CASTER Analysis conditions are as follows.
Cutoff energy: 600 eV
Brillouin zone sampling: Monkhorst-Pack method (2×3×2)
Used pseudo-potential: ultrasoft pseudopotential (Vanderbilt)
H atom: 1s1
Carbon atom: 2s2 2p2
Nitrogen atom: 2s2 2p3
Oxygen atom: 2s2 2p4
Iron atom: 3d6 4s2 and partial core correction method
Superexchange interaction: PBE (Perdew-Burke-Ernzerhof) method by GGA (generalized gradient approximation)
Effective coulomb interaction approximate parameter (U): U=5 eV relative to 3d orbital of iron atom
Solution of electronic state: Ensemble Density Functional Theory (EDFT)
Smearing parameter of Fermi energy: 0.1 eV
Crystal structure optimization method: Broyden-Fletcher-Goldfarb-Shanno (BFGS) method Regarding stability of the ferromagnetic substance, iron atom spin orientations (Fe1 (up), Fe2 (up), Fe3 (up), Fe4 (up)) of a ferromagnetic substance (Ferromagnetic) in FIG. 2 and iron atom spin orientations (Fe1 (up), Fe2 (down), Fe3 (up), Fe4 (down)) of an antiferromagnetic substance 1 (AF1) in FIG. 3, and iron atom spin orientations (Fe1 (down), Fe2 (up), Fe3 (down), Fe4 (up)) of an antiferromagnetic substance 2 (AF2) in FIG. 4 were calculated. The results were as illustrated in Table 1 and the ferromagnetic substance (Ferromagnetics) was most stable in terms of energy and an angle formed by Fe1 atom-O-Fe2 atom and Fe3 atom-O-Fe4 atom was 146.359°.

TABLE 1

Differences in Entire Energy of Electron System of Ferromagnetic and Antiferromagnetics (AF1 and AF2) (unit: eV)

|  | Ferromagnetic (Ferromagnetism) | Antiferromagnetic 1 (AF1) | Antiferromagnetic 2 (AF2) |
| --- | --- | --- | --- |
| Entire Energy of Electron System | −20940.116 | −20939.714 | −20940.039 |

Figure 2:
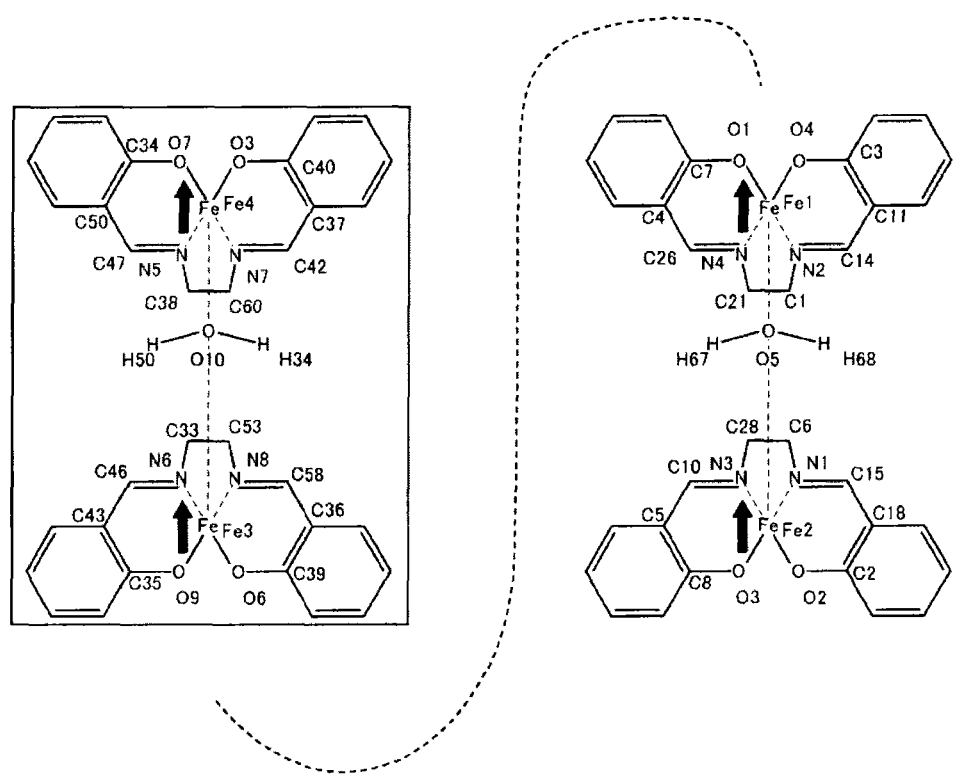
FIG. 2 is a molecular formula representing an iron atom spin orientation of a ferromagnetic substance (iron-salen complex compound)

When the electron spin orientations (directions indicated in FIGS. 2 to 4) of the respective iron-salen complex molecules are the same in the crystals of the compound composed of two iron-salen complex molecules, the ferromagnetic property of the metal complex compound is exhibited. The single crystal has a structure in which the metal complex compounds are layered. A dotted line in FIG. 2 represents that the metal complex compounds are layered one over the other.

We claim:

1. A ferromagnetic substance, comprising a crystal of a metal complex molecule in which a heterocycle is bonded to metal,
   wherein:
   the metal of the metal complex molecule is bonded to a metal of another metal complex molecule via oxygen as an electron donor;
   the metal complex molecule forms a single crystal whose average particle diameter is between 200 nm and 700 nm inclusive; and
   the ferromagnetic substance has a ferromagnetic property and crystal stability of the crystal based on a metal-electron donor-metal bond angle that is from 130° to 160°.

2. The ferromagnetic substance according to claim 1, wherein the electron donor comprises an element with an electron pair that can be donated to a metal atom of the metal complex molecule.

3. The ferromagnetic substance according to claim 1, wherein two molecules of the metal complex are bonded together via the electron donor by forming a coordinate bond of the metal and the electron donor.

4. The ferromagnetic substance according to claim 1, wherein the metal complex molecule forms the single crystal whose average particle diameter is between 300 nm to 600 nm inclusive.

5. The ferromagnetic substance according to claim 1, wherein the bond angle is within the range of 144° to 147°.

6. The ferromagnetic substance according to claim 1, wherein the metal complex molecule is a metal-salen complex molecule.

7. The ferromagnetic substance according to claim 1, wherein a distance between the metal and the oxygen is from 1.1 Å to 1.8 Å.

8. The ferromagnetic substance according to claim 6, wherein the metal-salen complex molecule is a bivalent iron-salen complex molecule.

9. A drug, comprising, as its principal component, a crystal of a metal complex molecule in which a heterocycle is bonded to metal,
   wherein:
   the metal of the metal complex molecule is bonded to a metal of another metal complex molecule via an electron donor;
   the metal complex molecule forms a single crystal whose average particle diameter is between 200 nm and 700 nm inclusive;
   the crystal has a ferromagnetic property based on a metal-electron donor-metal bond angle that is from 130° to 160°;
   the metal complex molecule is a metal-salen complex molecule;
   the electron donor is oxygen;
   a distance between the metal and the oxygen is from 1.1 Å to 1.8 Å; and
   the drug can be applied to an affected site with an external magnetic field.

* * * * *